United States Patent [19]

Hoefle et al.

[11] Patent Number: 4,714,762
[45] Date of Patent: Dec. 22, 1987

[54] ANTIARTERIOSCLEROTIC SUBSTITUTED BENZIMIDAZOL-2-YL-AND 3H-IMIDAZO[4,5-b]PYRIDIN-2-YL-PHENOXY-ALKANOIC ACIDS AND SALTS AND ESTERS THEREOF

[75] Inventors: Milton L. Hoefle, Ann Arbor; Ann Holmes, Dexter; Charlotte D. Stratton, Ann Arbor, all of Mich.

[73] Assignee: Warner-Lambert Company, Morris Plains, N.J.

[21] Appl. No.: 926,021

[22] Filed: Oct. 31, 1986

[51] Int. Cl.[4] .................... A61K 31/44; C07D 471/04; C07D 487/04

[52] U.S. Cl. .................................. 514/303; 514/394; 546/118; 548/333; 548/334

[58] Field of Search ................ 546/118; 548/333, 334; 514/303, 394

[56] References Cited

U.S. PATENT DOCUMENTS 3,674,836  7/1972  Creger ................................. 260/473
3,707,566  12/1972  Creger et al. ....................... 260/613

FOREIGN PATENT DOCUMENTS 2053215  2/1981  United Kingdom .

OTHER PUBLICATIONS

Gordon, T. et al., High Density Lipoprotein as a Protective Factor Against Coronary Heart Disease, May 1977, Amn. J. Med., 62, pp. 707–714, JAMA 251, pp. 361 and 365, 1984.

Primary Examiner—Henry R. Jiles
Assistant Examiner—Bernard I. Dentz
Attorney, Agent, or Firm—Elizabeth M. Anderson

[57] ABSTRACT

Novel substituted benzimidazol-2-yl-phenoxyalkanoic acids, salts and esters thereof and 3H-imidazo[4,5-b]pyridin-2-yl phenoxy-alkanoic acid, salts, and esters which are useful as antiarteriosclerotic agents are disclosed. The compounds elevate the high density lipoprotein fraction of cholesterol and also lower the low density lipoprotein fraction of cholesterol. Methods for preparing and using the compounds are included.

28 Claims, No Drawings

ANTIARTERIOSCLEROTIC SUBSTITUTED BENZIMIDAZOL-2-YL-AND 3H-IMIDAZO[4,5-b]PYRIDIN-2-YL-PHENOXY-ALKANOIC ACIDS AND SALTS AND ESTERS THEREOF

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-arteriosclerotic agents.

The compounds of the present invention are useful as anti-arteriosclerotic agents and are capable of elevating the high density lipoprotein fraction of cholesterol (HDL-C), and this effect is known to lower the risk factor of coronary heart disease (Gordon, T. et al., High Density Liproprotein as a Protective Factor Against Coronary Heart Disease, May 1977, The American Journal of Medicine, Vol. 62, pp. 707–714). There is strong support for the concept that induced lowering of the low density lipoprotein fraction of cholesterol (LDL-C) will reduce the risk for coronary heart disease in hypocholesteremic patients (JAMA 251:361 and 365, 1984). Certain compounds of the invention also are able to reduce the LDL-C, thus further reducing the risk factor of coronary heart disease.

British Pat. No. 2,053,215 covers certain benzimidazole derivatives of the structural formula

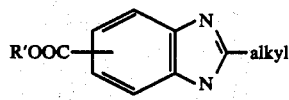

used as hypolipidemics.

One aspect of the present invention is a compound of the formula

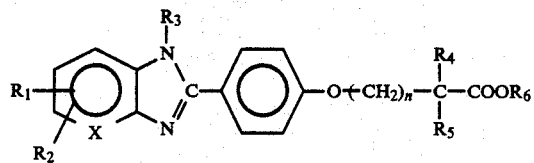

wherein X is CH or N; $R_1$ and $R_2$ are the same or different and are hydrogen, halogen, straight or branched alkyl or alkoxy of from one to six carbon atoms, or $CF_3$; n is an integer of from three to six; $R_4$ and $R_5$ are the same or different and are a straight or branched alkyl of from one to six carbon atoms or when $R_4$ and $R_5$ are taken together are $-(CH_2)_p$ wherein p is an integer of from two to five; $R_6$ is hydrogen, a straight or branched alkyl of from one to six carbon atoms, an alkali or alkaline earth metal cation, an organic amino cation, or ammonium; $R_3$ is hydrogen, an alkyl of from one to six carbon atoms which may be substituted by hydroxy, aryl, $CO_2R_6$ or the group

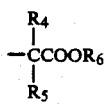

wherein $R_4$, $R_5$, and $R_6$ are as defined above; or a pharmaceutically acceptable acid addition salt thereof.

Another aspect of the present invention is a method of preparing a compound of formula I above which comprises reacting an optionally substituted benzimidazole phenol with a halogenated, alkyl-substituted carboxylic acid ester to produce the desired product and converting, if desired, to the pharmaceutically acceptable acid addition or base salts thereof.

Yet another aspect of the present invention is another method of preparing a compound of formula I above which comprises reacting a formylphenoxy substituted carboxylic acid ester with a substituted phenylene diamine to form the desired product and converting, if desired, to the pharmaceutically acceptable acid addition or base salts thereof.

A fourth aspect of the present invention is a pharmaceutical composition useful for treating arteriosclerosis in a mammal which comprises an effective amount of a compound of formula I above in combination with a pharmaceutically acceptable carrier in unit dosage form.

A fifth aspect of the present invention is a method of treating arteriosclerosis in mammals in need of such treatment which comprises administering an effective amount of the above defined pharmaceutical composition to said mammal.

DETAILED DESCRIPTION

This invention relates to compounds of formula I described above.

The compounds of the invention form pharmaceutically acceptable salts with both organic and inorganic acids. Examples of suitable acids for salt formation are hydrochloric, sulfuric, phosphoric, methanesulfonic and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention where $R_6$ is hydrogen form pharmaceutically acceptable salts with organic and inorganic bases. Examples of suitable bases for salt formation are sodium hydroxide, sodium carbonate, sodium bicarbonate, potassium hydroxide, calcium hydroxide, ammonia, organic amines and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purpose. The free acid forms differ from their respective salt forms somewhat in certain physical properties such as solubility in polar solvents, but the salts are otherwise equivalent to their respective free acid forms for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include fluorine, chlorine, bromine and iodine.

The alkyl and alkoxy groups contemplated by the invention, unless specified otherwise, comprise both straight and branched carbon chains of from one to about six carbon atoms. Representative of such groups are methyl, ethyl, isopropyl, butyl, pentyl, 3-methylpentyl, methoxy, ethoxy, i-propoxy, t-butoxy, n-hexoxy, 3-methylpentoxy and the like.

The preferred compounds of the invention are those wherein X is CH or N, $R_1$ and $R_2$ are the same or different and are hydrogen, halogen, or alkyl, $R_4$ and $R_5$ are the same or different and are an alkyl of from one to three carbon atoms, $R_6$ is hydrogen, or alkyl of from one to six carbon atoms, and n is an integer of from three to six.

The more preferred compounds of the present invention are those wherein X is CH, $R_1$ and $R_2$ are the same or different and are hydrogen or halogen, $R_4$ and $R_5$ are the same or different and are an alkyl of one or two carbon atoms, $R_6$ is hydrogen, or an alkyl of one or two carbon atoms, and n is an integer of from three to five.

Particularly valuable compounds of the present invention are:

5-[4-(1H-benzimidazol-2-yl)phenoxy]-2,2-dimethyl-pentanoic acid methyl ester,

5-[4-(1H-bezimidazol-2-yl)phenoxy]-2,2-dimethyl-pentanoic acid,

7-[4-(1H-benzmidazol-2-yl)phenoxy]-2,2-dimethyl-heptanoic acid methyl ester,

6-[4-(1H-benzimidazol-2-yl)phenoxy]-2,2-dimethyl-hexanoic acid methyl ester,

8-[4-(1H-benzimidazol-2-yl)phenoxy]-2,2- dimethyl octanoic acid methyl ester,

5-[4-(5-chloro-1H-benzimidazol-2-yl)phenoxy-2,2-dimethyl-pentanoic acid methyl ester, 5-[4-(5,6-dimethyl-1H-benzimidazol-2-yl) phenoxy)-2,2-dimethyl-pentanoic acid methyl ester, 7-[4-(5-chloro-1H-benzimidazol-2-yl)phenoxy-2,2-dimethyl-heptanoic acid methyl ester, 5-[4-(5,6-dichloro-1H-benzimidazol-2-yl) phenoxy)-2,2-dimethyl-pentanoic acid methyl ester, 2,2-dimethyl-5-[4-(1-methyl-1H-benzimidazol-2-yl)phenoxy]-pentanoic acid methyl ester, 2,2-dimethyl-5-[4-(1-methyl-1H-benzimidazol-2-yl)phenoxy]-pentanoic acid methyl ester, 2,[4-[(5-methoxy-4,4-dimethyl-5-oxopentyl)oxy]-phenyl]-1H-benzimidazole-1-acetic acid ethyl ester, 2,2-dimethyl-5-[4-[1-(phenylmethyl)-1H-benzimidazol-2-yl]phenoxy]-pentanoic acid methyl ester, 5-[4-[1-(2-hydroxyethyl)-1-H-benzimidazol-2-2-yl]-phenoxy]-2,2-dimethyl-pentanoic acid hydrate, 2,2-dimethyl-5-[4-[1-(1-methylethyl)-1H-benzimidazol-2-yl]phenoxy]-pentanoic acid, 2-[4-[(4-carboxy-4-methylpentyl)oxy)phenyl]-α,α-dimethyl-1H-benzimidazole-1-pentanoic acid, 2,2-dimethyl-7-[4-[1-(phenylmethyl)-1H-benzimidazol-2-yl]phenoxy]-heptanoic acid methyl ester, 5-[4-(3H-imidazo[4,5-b]pyridin-2-yl)phenoxy]-2,2-dimethyl-pentanoic acid methyl ester, 5-[4-(3H-imidazo[4,5-b]pyridin-2-yl)phenoxy]-2,2-dimethyl-pentanoic acid.

Scheme I below is a general flow chart for the preparation of the compounds of the present invention. Part A refers to Examples 1 and 4–11. Part B refers to Examples 2 and 19. Part C illustrates Examples 12–18. Part D shows the process of Examples 3 and 20 specifically, and is a step in Examples 15, 16, and 17.

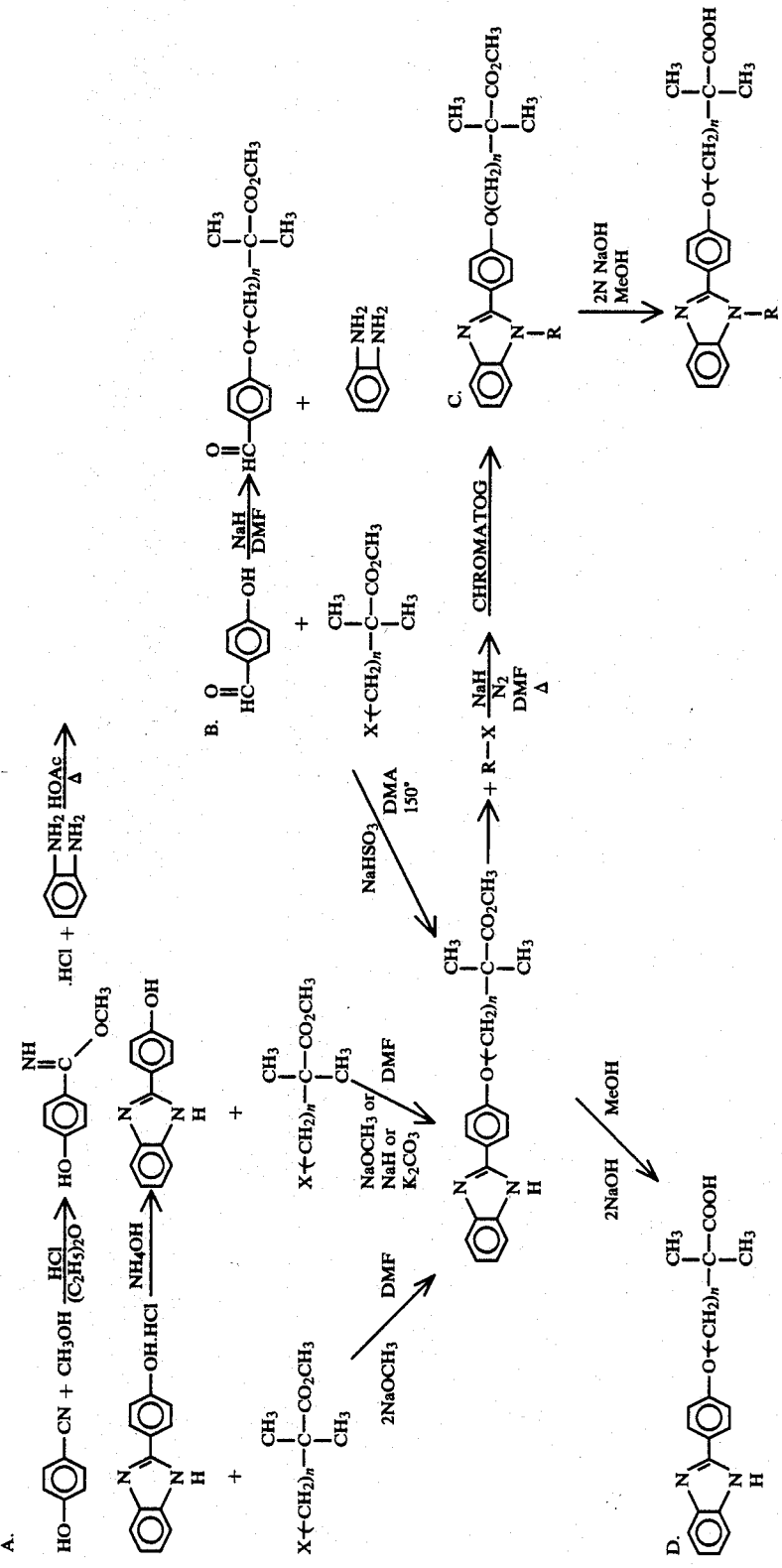

In part A of Scheme I, compounds of formula I where R₆, as defined above is other than H, are prepared by reacting a benzimidazolephenol hydrochloride with a halogen substituted carboxylic acid ester. Examples of such esters are methyl-7-iodo-2,2-dimethyl heptanoate, methyl 6-iodo-2,2-dimethylhexanoate, methyl 8-bromo-2,2-dimethylpentanoate, methyl 7-bromo-2,2-dimethyl-heptanoate, methyl 5-bromo-2,2-dimethylpentanoate and the like. Some examples of solvents suitable for use in the reaction are diethyl ether, tetrahydrofuran, dimethylformamide, dimethyl sulfoxide, and the like. A preferred solvent is dimethylformamide. Two equivalents of sodium methoxide is dissolved together with the phenol hydrochloride with dimethylformamide. In general the reaction is carried out at temperatures between 80° and 120° C.; the preferred temperature range is from 90° to 110° C. The reaction proceeds for from four to eight hours, preferably for from five to seven hours.

Alternatively in Part A of Scheme I, compounds of formula I are produced by reacting a benzimidazole phenol with a halogen substituted carboxylic acid ester. Equimolar amounts of sodium methoxide are used, other reaction conditions do not change appreciably.

The benzimidazole phenol hydrochloride is produced by reacting a benzene carboximidoic acid, 4-hydroxymethyl ester hydroxyloride with an o-phenylene-diamine at reflux in glacial acetic acid.

In Part B Scheme I, compounds of formula 1 were R₆ is as described hereinabove except when R₆ is H are prepared by reacting a formylphenoxycarboxylic acid ester with o-phenylenediamine. The reaction takes place in a high boiling solvent such as dimethylacetamide. The reaction takes place in the presence of sodium hydrogen sulfite. The reaction produced at temperatures of from 130° to 180° C. for from one to four hours. Preferred conditions are a temperature of from 150° to 170° C. for from two to three hours.

The formylphenoxycarboxylic acid ester is prepared by reacting 4-hydroxybenzaldehyde with a halogenated carboxylic acid ester.

In Part C of Scheme I compounds of formula I wherein R₆ is an alkyl of from one to six carbon atoms are treated with a halogenated organic compound, R₃Y, (wherein Y is halogen, chloride, fluoride, bromide or iodide, the halide of choice with vary with the R₃ moiety; preferred usually are bromide or iodide) to form the corresponding N-substituted compounds of formula I where R₃ is an alkyl of from one to six carbon atoms which may be substituted by hydroxy, aryl, $CO_2R_6$ or the group

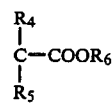

where $R_4$, $R_5$, and $R_6$ are defined hereinabove. The reaction is conveniently carried out in a solvent such as diethyl ether, tetrahydrofuran, dimethylformamide and the like. Especially preferred is the dimethylformamide. The reaction is carried out in the presence of sodium hydride. The unreacted starting material is separated from the products to column chromatography. The time and temperature of the reaction are not critical, rather they depend somewhat upon the reactants involved. The temperatures can vary from about 25° C. to about 120° C., preferably from about 35° to 100° C. The reaction time is from about one to three hours.

In Part D of Scheme I esters of formula I where R₆ is an alkyl from one to six carbon atoms are converted to the free carboxylic acid by reaction with a strong base. Suitable strong bases include sodium hydroxide, sodium carbonate, sodium bicarbonate, potassium hydroxide, calcium hydroxide, and the like. Especially suitable is NaOH or potassium hydoxide. This hydrolysis reaction is conveniently carried under reflux in solvents such as methanol ethanol and the like. Methanol is especially suitable. The reaction proceeds from one to four hours; preferably for from two to three hours.

The compounds of the invention are new chemical substances of value as pharmacological agents for the treatment of arteriosclerosis in warm-blooded animals. The anti-arteriosclerotic activity of representative compounds of the invention was established by the screening procedure described in Maxwell, R. E., Nawrocki, J. W., and Uhlendorf, P. D., Artery, 1, 303 (1978). This procedure is incorporated by reference herein. Utilizing this procedure, the following results were obtained for representative compounds of this invention. See Table 1 below.

TABLE 1

| Example Number | $R_1$ | $R_2$ | $R_3$ | $R_6$ | n | Elevation* HDL-C | Reduction* LDL-C |
|---|---|---|---|---|---|---|---|
| 1 | H | H | H | Me | 3 | .49 | — |
| 3 | H | H | H | H | 3 | .22 | .51 |
| 12 | H | H | $CH_3$ | Me | 3 | .75 | .95 |
| 13 | H | H | $CH_2CO_2Et$ | Me | 3 | .06 | — |
| 14 | H | H | $CH_2Ph$ | Me | 3 | .97 | 1.0 |
| 15 | H | H | $-C_2H_4OH$ | H | 3 | .33 | .55 |
| 16 | H | H | $-CH(CH_3)_2$ | H | 3 | .40 | .59 |
| 17 | H | H | $-(CH_2)_3C(CH_3)_2CO_2H$ | H | 3 | .85 | .92 |
| 4 | H | H | H | Me | 5 | 1.6 | .85 |
| 5 | H | H | H | Me | 4 | 1.0 | .58 |
| 6 | H | H | H | Me | 6 | .73 | .56 |
| 7 | H | 5-Cl | H | Me | 3 | .89 | .85 |
| 8 | 6-$CH_3$ | 5-$CH_3$ | H | Me | 3 | .52 | .31 |
| 9 | H | 5-Cl | H | Me | 5 | .75 | 1.0 |
| 10 | 6-Cl | 5-Cl | H | Me | 3 | .91 | .45 |
| 11 | H | 5-$CH_3$ | H | Me | 3 | .75 | .70 |
|  |  |  | H | Me | 3 | .58 | .48 |

TABLE 1-continued

| Example Number | R₁ | R₂ | R₃ | R₆ | n | Elevation* HDL-C | Reduction* LDL-C |
|---|---|---|---|---|---|---|---|
| 18 | H | H | CH$_2$C$_6$H$_5$ | Me | 5 | .55 | .83 |

*The elevation of HDL-C and the reduction of LDL-C is expressed as a ratio of effect of the test compound with the effect of gemfibrozil which was used as a control in this test. Gemfibrozil has been shown to elevate HDL and to lower LDL in man. [Manninen, Vesa, The Gemfibrozil Study, 1985, Acta Med. Scand. (Supplement), Vol. 701, pp 83–89.]

The compounds of the invention can be prepared and administered in a wide variety of oral and parenteral dosage forms. It will be clear to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceytically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation; for example, packeted tablets, capsules and powders in vials or ampules. The unit dosage form can also be a capsule, cachet or tablet itself or it can be the appropriate number of any of these packaged form.

The quantity of active compound in a unit dose of preparation may be varied or adjusted from 1 mg to 100 mg according to the particular application and the potency of the active ingredient.

In therapeutic use as agents for treating arteriosclerosis the compounds utilized in the pharmaceutical method of this invention are administered at the initial dosage of about 10 mg to about 250 mg per kilogram daily. A daily dose range of about 10 mg to about 30 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The compounds of the present invention are useful as anti-arteriosclerotic agents. These compounds elevate the high density lipoprotein fraction of cholesterol and also lower the low density lipoprotein fraction of cholesterol.

The following examples are provided to enable one skilled in the art to practice the present invention. These examples are not intended to limit the scope of the invention, but are to be illustrative thereof.

EXAMPLE 1

Pentanoic acid, 5-[4-(1H-benzimidazol-2-yl)phenoxy]-2,2-dimethyl-, methyl ester Route A A mixture of 324 g (0.3 mol) of o-phenylenediamine, 67.5 g (0.36 mol) of benzene carboximidoic acid, 4 hydroxy-, methyl ester hydrochloride and 450 ml of glacial acetic acid was stirred at reflux for two hours. After standing overnight at room temperature the hydrochloride salt of the benzimidazole was collected by filtration, washed with acetic acid, and finally ether. The hydrochloride salt of the product was suspended in 450 ml of dilute ammonium hydroxide, stirred for one hour at room temperature, and chilled briefly. The product was collected and the filter cake was treated with charcoal during recrystallization from a 2:1 water-alcohol mixture. Filtration gave 45.9 g (73%) of 4-(1H-benzimidazol-2-yl)phenol (mp 286°–289° C.) and a second crop of 2.8 g on standing.

Anal. Calcd. for C$_{13}$H$_{10}$N$_2$O: C, 74.27; H, 4.79; N, 13.33. Found: C, 74.10; H, 4.82; N, 13.36.

A mixture of 52.6 g (0.25 mol) of 4-(1H-benzimidazol-2-yl) phenol and 13.5 g (0.25 mol) of sodium methoxide in 600 ml of dimethylformamide was stirred on the steam bath. To this was added dropwise 55.8 g (0.25 mol) of methyl 5-bromo-2,2-dimethylpentanoate. The resulting mixture was stirred on the steam bath for six hours and allowed to stand at room temperature overnight. The dimethylformamide was removed on the rotary evaporator and the residue was dissolved in a mixture of water and ethyl acetate. The aqueous layer was further extracted with a mixture of ethyl acetate-chloroform. The combined solvent layers were washed with dilute sodium hydroxide until the wash remained strongly basic. Unreacted starting benzimidazole was recovered from the aqueous layer. The solvent layer was washed with water several times until neutral, dried over magnesium sulfate, and concentrated to 300 ml. Isopropyl ether was added to a volume of 800 ml. After chilling, the product was filtered, washed, and dried; wt 48.5 g (55%); mp 105°–107.5° C. Two recrystallizations from ethyl acetate-isopropyl ether yielded 46.9 g (53%) of the purified product; mp 166.5°–168° C.

Anal. Calcd. for $C_{21}H_{24}N_2O_3$: C, 71.57; H, 6.86; N, 7.95. Found: C, 71.53; H, 6.84; N, 7.83.

EXAMPLE 2

Pentanoic acid,
5-[4-(1H-benzimidazol-2-yl)phenoxy]-2,2-dimethyl-, methyl ester Route B A solution of 48.9 g (0.4 mol) of 4-hydroxybenzaldehyde in 600 ml of dimethylformamide was stirred under a nitrogen atmosphere. Sodium hydride (31.2 g; 0.44 mol) was added to the stirring solution over 45 minutes. The temperature of the reaction mixture was maintained at 35°–40° during the addition, and stirring was continued for an additional 45 minutes at room temperature. Methyl 5-bromo-2,2-dimethylpentanoate (98.1 g; 0.44 mol), was added dropwise over 20 minutes. The reaction temperature was maintained at 40° during the addition. After addition was complete, the temperature was raised to 65° C. and stirring was continued at 65° C. for 3½ hours. After standing overnight, the dimethylformamide was removed on a rotary evaporator and the residue was taken up in water and ether. The aqueous layer was extracted a second time with ether and the combined extracts were washed, dried, and concentrated under reduced pressure. The residue was triturated two times with n-heptane. The heptane insoluble oil was distilled via a short path apparatus to give methyl 5-[4-formylphenoxy)-2,2-dimethyl-pentanoate: bp 143°–144° C. at 0.03 mm of Hg; yield 39.4 g (37%). Additional analytically pure product was obtained from the heptane extract: 32.3 g (31%). Anal. Calcd. for $C_{15}H_{20}O_4$:

C, 68.16; H, 7.63. Found: C, 68.18; H, 7.49.

A stirred mixture of 540 mg (5 mmol) of o-phenylenediamine, 1.32 g (5 mmol) of methyl 5-[4-formylphenoxy)-2,2-dimethylpentanoate and 1.56 g of sodium hydrogen sulfite in 12 ml of dimethylacetamide was placed in an oil bath maintained at 160° and heated for two hours. The cooled reaction mixture was poured into 75 ml of water and chilled. The gummy solid was collected and recrystallized first from 50% aqueous ethanol and finally from a mixture of ethyl acetate and isopropyl ether to yield the product; wt 1.44 g (82%); mp 166.5°–167.5° C.

Anal. Calcd. for $C_{21}H_{24}N_2O_3$: C, 71.57; H, 6.86; N, 7.95. Found: C, 71.25; H, 6.71; N, 7.78.

EXAMPLE 3

Pentanoic acid,
5[4-(1H-benzimidazol-2-yl)phenoxy]-2,2-dimethyl-

Pentanoic acid, 5-[4-(1H-benzimidazol-2-yl) phenoxy]-2,2-dimethyl-, methyl ester (3.5 g; 0.01 mol), and 25 ml of 2 N sodium hydroxide in methanol were stirred and heated at reflux for three hours. The methanol was removed at reduced pressure and the residue was dissolved in water and then acidified with dilute aqueous acetic acid. The mixture was stirred at room temperature for one hour, chilled and filtered to yield the crude product which was recrystallized two times from aqueous alcohol: 2.55 g (75%); mp 263°–264.5° C.

Anal. Calcd. for $C_{20}H_{22}N_2O_3$: C, 70.99; H, 6.55; N, 8.28. Found: C, 70.82; H, 6.58; N, 8.26.

EXAMPLE 4

Heptanoic acid,
7-[4-(1H-benzimidazol-2-yl)phenoxy]-2,2-dimethyl-, methyl ester

Heptanoic acid, 7-[4-(1H-benzimidazol-2-yl) phenoxy]-2,2-dimethyl, methyl ester was prepared by the method described in Example 1 from the following starting materials: 4-(1H-benzimidazol-2-yl)phenol (2.84 g; 13.5 mmol), methyl 7-iodo-2,2-dimethyl-heptanoate heptanoate (4.03 g; 13.5 mmol), sodium methoxide (730 mg; 13.5 mmol) and 36 ml of dimethylformamide. The crude product was chromatographed on a silica gel column (2% methanol in methylene chloride) and crystallized from a mixture of ethyl acetate and isopropyl ether to give 1.86 g of pure product; mp 193.5°–194.5° C.

Anal. Calcd. for $C_{23}H_{28}N_2O_3$: C, 72.61; H, 7.42; N, 7.36. Found: C, 72.24; H, 7.39; N, 7.29.

EXAMPLE 5

Hexanoic acid,
6-[4-(1H-benzimidazol-2-yl)phenoxy]-2,2-dimethyl-, methyl ester

Hexanoic acid, 6-[4-(1H-benzimidazol-2-yl) phenoxy]-2,2-dimethyl, methyl ester was prepared by the method described in Example 1 from the following: 4-(1H-benzimidazol-2-yl)phenol (3.89 g; 18.5 mmol), methyl 6-iodo-2,2-dimethyl hexanoate (5.26 g; 18.5 mmol), sodium methoxide (1 g; 18.5 mmol) and 50 ml of dimethylformamide. The crude product was crystalized from ethyl acetate-isopropyl ether. Final purification was accomplished by silica gel, column chromatography (2% methanol in methylene chloride) and finally crystallization from ethyl acetate-hexane: yield 2.2 g, mp 159.5°–160.5° C.

Anal. Calcd. for $C_{22}H_{26}N_2O_3$: C, 72.11; H, 7.15; N, 7.64. Found: C, 72.23; H, 7.04; N, 7.59.

EXAMPLE 6

Octanoic acid, 8-[4-(1H-benzimidazol-2-yl)phenoxy]-2, 2-dimethyl-, methyl ester

This compound was prepared by the method described in Example 1 from the following starting materials: 4-(1H-benzimidazol-2-yl)phenol (4.2 g; 20 mmol), methyl 8-bromo-2,2-dimethyloctanoate (5.3 g; 20 mmol), sodium methoxide (1.08 g; 20 mmol) and 50 ml of dimethylformamide. The crude product was crystallized from ethyl acetate-isopropyl ether, dissolved in 4% methanol in methylene chloride, and filtered through a coarse sintered glass funnel containing silica gel. Evaporation of the solvent and recrystallization from ethyl acetate-hexane gave 2.45 g of pure product; mp 163.5°-164.5° C.

Anal. Calcd. for $C_{24}H_3N_2O_3$: C, 73.07; H, 7.66; N, 7.10. Found: C, 73.26; H, 7.58; N, 7.18.

EXAMPLE 7

Pentanoic acid, 5-[4-(5-chloro-1H-benzimidazol-2-yl) phenoxy]-2,2-dimethyl-, methyl ester This compound was prepared by the method described in Example 1. The following reactants and quantities are employed: 4-(5-chloro-1H-benzimidazol-2-yl)phenol (6.12 g; 25 mmol), methyl S-bromo-2,2-dimethylpentanoate (5.58 g; 25 mmol), sodium methoxide (1.35 g; 25 mmol) and 65 ml of dimethylformamide. The benzimidazole was prepared as in Example 1 (Route A) from 4-chlorophenylenediamine. The crude product was purified by multiple recrystallizations from chloroform-hexane and ethyl acetate-isopropyl ether and column chromatography over silica gel (2% methanol in methylene chloride). Final crystallization from ethyl acetate-hexane and filtration through a coarse sintered glass funnel with Celite pad gave pure product; 2.45 g, mp 133.5°-134.5° C.

Anal. Calcd. for $C_{21}H_{23}Cl N_2O_3$: C, 65.19; H, 5.99; N, 7.24; Cl, 9.16. Found: C, 65.31; H, 6.09; N, 7.08; Cl, 9.44.

EXAMPLE 8

Pentanoic acid, 5-[4-(5,6-dimethyl-1H-benzimidazol-2-yl) phenoxy]-2,2-dimethyl-, methyl ester This compound was prepared by a modification of the method used in Example 1. The starting benzimidazole was used as the hydrochloride and two equivalents of sodium methoxide were employed. The following starting materials were used: 4-(5,6-dimethyl-1H-benzimidazol-2-yl) phenol hydrochloride (6.87 g; 25 mmol), methyl 5-bromo-2,2-dimethylpentanoate (5.57 g; 25 mmol), sodium methoxide (2.7 g; 50 mmol) and 60 ml of dimethylformamide. The benzimidazole hydrochloride was prepared as in Example 1 (Route A) from 4,5-dimethylphenylenediamine. Crude product was obtained by recrystallization from ethyl acetate-isopropyl ether: 2.52 g; mp 85°-88° C. Silica gel column chromatography (2% methanol in methylene chloride and methylene chloride:methanol, (12:1)), and final recrystallization from ethyl acetate with charcoal treatment yielded 1.26 g of pure product; mp 148.5°-149.5° C.

Anal. Calcd. for $C_{23}H_{28}N_2O_3$: C, 72.61; H, 7.42; N, 7.36. Found: C, 72.36; H, 7.52; N, 7.13.

EXAMPLE 9

Heptanoic acid, 7-[4-(5-chloro-1H-benzimidazol-2-yl) phenoxy]-2,2-dimethyl, methyl ester This compound was prepared by the method described in Example 1 except potassium carbonate was used in place of sodium methoxide. The following reactants and quantities were used: 4-(5-chloro-1H-benzimidazol-2-yl) phenol (6.73 g; 27.5 mmol), methyl 7-bromo-2,2-dimethylheptanoate (6.91 g; 27.5 mmol), anhydrous potassium carbonate (4.37 g; 31.6 mmol) and 50 ml of dimethylformamide. The benzimidazole was prepared as in Example 1 (Route A) from 4-chloro-phenylenediamine. The crude product was purified by silica gel column chromatography (3% methanol in methylenechloride) and crystallization from a mixture of ethyl acetate-hexane to give 2.38 g of pure product; mp 144°-145.5° C.

Anal. Calcd. for $C_{23}H_{27}ClN_2O_3$: C, 66.58; H, 6.56; N, 6.75; Cl, 8.54. Found: C, 66.60; H, 6.33; N, 6.65; Cl, 8.66.

EXAMPLE 10

Pentanoic acid, 5-[4-(5,6-dichloro-1H-benzimidazol-2-yl) phenoxy]-2,2-dimethyl-, methyl ester This compound was prepared by the method used in Example 1. The following reactants and quantities were used: 4-(5,6-dichloro-1H-benzimidazol-2-yl) phenol (7.81 g; 28 mmol), methyl 5-bromo-2,2-dimethylpentanoate (6.25 g; 28 mmol), anhydrous potassium carbonate (4.45 g; 32.2 mmol) and 40 ml of dimethylformamide. The benzimidazole was prepared as in Example 1 (Route A) from 4,5-dichloro-O-phenylenediamine. The crude material was recrystallized two times from ethyl acetate-isopropyl ether and finally two times from ethyl acetate to yield pure product: wt 3.11 g; mp 177°-178° C.

Anal. Calcd. for $C_{21}H_{22}Cl_2N_2O_3$: C, 59.87; H, 5.26; N, 6.65; Cl, 16.83. Found: C, 59.88; H, 5.14; N, 6.57; Cl, 17.10.

EXAMPLE 11

Pentanoic acid, 2,2-dimethyl-5-[4-(5-methyl-1H-benzimidazol-2-yl) phenoxy]-, methyl ester, hydrate (10:3)

This compound was also prepared by the method used in Example 1. The following materials were used: 4-(5-methyl-1H-benzimidazol-2-yl)phenol (6.73 g; 30 mmol), methyl 5-bromo-2,2-dimethylpentanoate (6.69 g; 30 mmol), and 40 ml of dimethylformamide. The benzimidazole was prepared by the method of Example 1 (Route A) from 3,4-diamino toluene. The crude product was purified by silica gel column chromatography and recrystallization from ethyl acetate-hexane yielded 2.77 g of a hydroscopic product. Analytically pure material was obtained when a sample was dried overnight under vacuum at 50° C.; mp 72.5°-74.5° C.

Anal. Calcd. for $C_{22}H_{26}N_2O_3$: C, 72.11; H, 7.15; N, 7.64. Found: C, 72.11; H, 7.30; N, 7.57.

More stable material was obtained by allowing the product to be exposed to the atmosphere for five days; mp 58°-62° C.

Anal. Calcd. for $C_{22}H_{26}N_2O_3 \cdot 3H_2O$ C, 71.06; H, 7.21; N, 7.53; $H_2O$, 1.45. Found: C, 71.32; H, 7.43; N, 7.38; $H_2O$, 1.72.

EXAMPLE 12

Pentanoic acid, 2,2-dimethyl-5-[4-(1-methyl-1H-benzimidazol-2-yl)phenoxyl]-, methyl ester Pentanoic acid, 5-[4-(1H-benzimidazol-2-yl) phenoxy]-2,2-dimethyl-, methyl ester (5.29 g; 15 mmol) was dissolved in 15 ml of dimethylformamide. To the stirred solution under an atmosphere of nitrogen was added 50% sodium hydride (721 mg; 15 mmol) in portions over 15 minutes while the temperature was maintained below 40°. The last sodium hydride was washed into the reaction mixture with 3-5 ml of toluene. Stirring was continued at 35°-40° for 75 minutes. Methyl iodide (2.13 g; 15 mmol) in 1.5 ml of toluene was added dropwise over 25 minutes while the temperature was maintained at less than 35° C. Stirring under nitrogen was continued for 30 minutes, temperature was then raised to 53° for 20 minutes and finally maintained at steam bath temperature for 30 minutes. After standing at room temperature overnight the precipitate was removed by filtration. The residue was taken up in chloroform, washed with water, dried, and evaporated to an oil which solidified on standing. Three recrystallizations from isopropanol gave 2.84 g; mp 103.5°–104.5° C. Silica gel column chromatography (2% methanol in methylene chloride) separated the unreacted starting material yielding 2.48 g of product which on recrystallization from isopropanol-isopropyl ether gave 2.12 g of pure product; mp 105°–106.2° C.

Anal. Calcd. for $C_{22}H_{26}N_2O_3$: C, 72.11; H, 7.15; N, 7.64. Found: C, 71.96; H, 7.06; N, 7.55.

EXAMPLE 13 1H-Benzimidazole-1-acetic acid, 2-[4-[(5-methoxy-4,4-dimethyl-5-oxopentyl)oxy]-phenyl]-, ethyl ester This compound was prepared by the procedure described in Example 12 from the following: pentanoic acid, 5-[4-(1H-benzimidazol-2-yl)phenoxy]-2,2-dimethyl-, methyl ester (5.29 g; 15 mmol), 50% sodium hydride (721 mg; 15 mmol), 5 ml of toluene, ethyl bromo acetate (2.5 g; 15 mmol) and 15 ml of dimethylformamide. Two crystallizations from isopropyl ether gave 3.48 g of crude product; mp 79°–80° C. Silica gel column chromatography and recrystallization from isopropyl ether yielded 3.23 g of pure product; mp 79.5°–81° C.

Anal. Calcd. for $C_{25}H_{30}N_2O_5$: C, 68.47; H, 6.90; N, 6.39. Found: C, 68.43; H, 6.81; N, 6.38.

EXAMPLE 14

Pentanoic acid, 2,2-dimethyl-5-[4-(1-(phenylmethyl)-1H-benzimidazol-2-yl]phenoxy]-, methyl ester This compound was prepared by the method used in Example 12 from the following starting materials: pentanoic acid, 5'[4-(1H-benzimidazol-2-yl)phenoxy]-2,2-dimethyl-, methyl ester (5.29 g; 15 mmol), 50% sodium hydride (721 mg; 15 mmol), 7 ml of toluene, benzylbromide (2.56 g; 15 mmol), and 15 ml dimethyl formamide. The crude product was crystallized from isopropyl ether: wt 4.87 g; mp 104.5°–105.5° C. A chloroform solution of the product was washed with 1 N sodium hydroxide, washed with water to neutrality, dried, and the chloroform was removed under reduced pressure. After two recrystallizations from isopropyl ether-chloroform, pure product was obtained: wt 3.87 g; mp 106.5°–107.5° C.

Anal. Calcd. for $C_{28}H_{30}N_2O_3$: C, 75.99; H, 6.83; N, 6.33. Found: C, 75.68; H, 6.52; N, 6.21.

EXAMPLE 15

Pentanoic acid, 5-[4-[1-(2-hydroxyethyl)-1H-benzimidazol-2-yl]phenoxy]-2,2-dimethyl-, 0.33 hydrate This compound was prepared by the general method described in Example 12 from the following: pentanoic acid, 5-[4-(1H-benzimidazol-2-yl)phenoxy]-2,2-dimethyl-, methyl ester (10.58 g; 30 mmol), 50% sodium hydride (1.44 g; 30 mmol), 14 ml of toluene, 2-bromoethanol (3.75 g; 30 mmol) and 30 ml of dimethylformamide. The reaction mixture was heated a total of 2¾ hours on the steam bath. After the usual workup the residue was triturated with ether to give 4.5 g of crude starting material. The filtrate was concentrated and the residue was purified by repeated silica gel column chromatography (2% methanol in methylene chloride) to give 2.78 g (7 mmol) of the ester. The ester was hydrolyzed by heating at reflux for two hours with 34.5 ml of 2 N sodium hydroxide in methanol. Methanol was removed under reduced pressure, the residue was suspended in water and the cooled solution was acidified with glacial acetic acid. The product was collected, washed with water, and air dried to yield 2.31 g; mp 156°–157.5° C. Two recrystallizations from aqueous alcohol yield 1.97 g of product; mp 158.5°–159.5° C. (shrinks at 140° C.).

Anal. Calcd. for $C_{22}H_{26}N_2O_4.\frac{1}{3}H_2O$:
C, 68.02; H, 6.92; N, 7.21; $H_2O$, 1.55. Found: C, 67.85; H, 6.86; N, 7.28; $H_2O$, 1.32.

EXAMPLE 16

Pentanoic acid, 2,2-dimethyl-5[4-[1-methylethyl)-1H-benzimidazol-2-yl]phenoxy]-

This compound was prepared by the general method described in Example 12 from the following: pentanoic acid, 5-[4-(1H-benzimidazol-2-yl) phenoxy]-2,2-dimethyl-, methyl ester (5.29 g; 15 mmol), 50% sodium hydride (721 mg; 15 mmol), 7 ml of toluene, 2-bromopropane (3 g; 24.4 mmol) and 15 ml of dimethylformamide. The crude material obtained after the usual work up was triturated with 100 ml of ether, which on filtration gave 3.69 g of starting material; mp 165.6°–166.5°. The filtrate was concentrated to give 2.2 g of crude material which was purified by chromatography over silica gel columns (2% methanol in methylene chloride). The purest material (1 g) was hydrolyzed as in Example 15 by heating at reflux for three hours with 6.4 ml of 2 N sodium hydroxide in methanol. The usual work up and two recrystallizations from aqueous ethanol gave 786 mg of pure product; mp 210.5°–211.5° C.

Anal. Calcd. for $C_{23}H_{28}N_2O_3$: C, 72.61; H, 7.42; N, 7.36. Found: C, 72.38; H, 7.36; N, 7.25.

EXAMPLE 17

1H-Benzimidazole-1-pentanoic acid, 2[4-[(4-carboxy-4-methylpentyl)oxy]phenyl]-α,α-dimethyl- This compound was prepared by the usual procedure described in Example 12 from the following: pentanoic acid, 5[4-(1H-benzimidazol-2-yl)phenoxy]-2,2-dimethyl-, methyl ester (5.29 g; 15 mmol), 50% sodium hydride (721 mg; 15 mmol), 5 ml of toluene, methyl 5-bromo-2,2-dimethylpentanoate (3.35 g; 15 mmol) and 15 ml of dimethylformamide. The crude product was purified by silica gel column chromatography (1% and 2% methanol methylene chloride) to give 6.35 g of slightly impure product diester. This ester (5.14 g) was hydrolyzed by the usual method described in Example 15 employing 2 N methanolic sodium hydroxide. The methanol was removed under reduced pressure and the residue was dissolved in water. As soon as solution was complete a precipitate forms and the mixture was chilled. The precipitate was collected, redissolved in water with warming and finally the cooled solution was acidified with acetic acid and the product precipitated. Recrystallization from a dimethylformamide-water mixture (1:2) gave 3.7 g of pure product; mp 203.5°–204.5° C.

Anal. Calcd. for $C_{27}H_{34}N_2O_5$: C, 69.51; H, 7.35; N, 6.00. Found: C, 69.32; H, 7.14; N, 5.95.

EXAMPLE 18

Heptanoic acid, 2,2-dimethyl-7-[4-[1-(phenylmethyl)-1H-benzimidazol-2-yl]phenoxy]-, methyl ester This compound was prepared by the method described in Example 12 from the following: heptanoic acid, 7-[4-(1H-benzimidazol-2-yl)phenoxy]-2,2-dimethyl-, methyl ester (2.56 g; 6.7 mmol), 50% sodium hydride (3.23 mg; 6.7 mmol), benzyl bromide (1.15 g; 6.7 mmol) in 2 ml of toluene and 9 ml of dimethylformamide. Recrystallizations from isopropyl ether-hexane and isopropyl ether gave 1.88 g of crude product; mp 86°–87.5° C. Further purification was achieved by silica gel column chromatography (2% methanol in methylene chloride) and crystallization from isopropyl ether-hexane to give pure product: 1.59 g; mp 88.5°–89.5° C.

Anal. Calcd. for $C_{30}H_{34}N_2O_3$: C, 76.57; H, 7.28; N, 5.95. Found: C, 76.66; H, 7.16; N, 5.77.

EXAMPLE 19

Pentanoic acid, 5-[4-(3H-imidazo[4,5-b]pyridin-2-yl)phenoxy]-2,2-dimethyl-, methyl ester This compound was prepared by the method described in Example 1 (Route B) from the following: 2,3-diaminopyridine (1.09 g; 10 mmol), methyl 5-[4-formylphenoxy)-2,2-dimethyl-pentanoate (2.64 g; 10 mmol), sodium hydrogen sulfite (1.56 g; 15 mmol) and 12 ml of dimethylacetamide. The crude product was recrystallized from 50% aqueous alcohol and finally was treated with charcoal and recrystallized from 95% alcohol to yield 2.81 g (80%) of pure product; mp 181°–183° C.

Anal. Calcd. for $C_{20}H_{23}N_3O_3$: C, 67.97; H, 6.56; N, 11.89. Found: C, 67.68; H, 6.61; N, 11.75.

EXAMPLE 20

Pentanoic acid, 5-[4-(3H-imidazo[4,5-b]pyridin-2-yl)phenoxy]-2,2-dimethyl-

Pentanoic acid, 5-[4-(3H-imidazo[4,5-b]pyridin-2-yl)phenoxy]-2,2-dimethyl-, methyl ester (2.51 g; 7.1 mmol) and 18 ml of 2 N sodium hydroxide in methanol were combined and heated at reflux with stirring for three hours. The methanol was removed under reduced pressure, the residue was dissolved in 25 ml of water, and the cooled solution was acidified with glacial acetic acid to precipitate the crude product: wt 2.33 g; mp 254.5°–256.5° C. Recrystallizations from aqueous alcohol-dimethylfomamide and acetonitrole-dimethylformamide mixtures and treatment with charcoal gave 1.8 g of pure product; mp 256°–257° C. (If the melting point was taken too rapidly a crystal form change was apparent at 245° C.) The analytical sample was dried under vacuum at 100°.

Anal. Calcd. for $C_{19}H_{21}N_3O_3$: C, 67.24; H, 6.24; N, 12.38. Found: C, 67.02; H, 6.32; N, 12.34.

We claim:

1. A compound having the structural formula

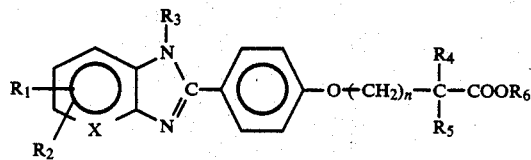

wherein X is CH or N; $R_1$ and $R_2$ are the same or different and are hydrogen, halogen, straight or branched alkyl or alkoxy of from one to six carbon atoms, or $CF_3$; n is an integer of from three to six; $R_4$ and $R_5$ are the same or different and are a straight or branched alkyl of from one to six carbon atoms or when $R_4$ and $R_5$ are taken together are $-(CH_2)_p$ wherein p is an integer of from two to five; $R_6$ is hydrogen, a straight or branched alkyl of from one to six carbon atoms, an alkali or alkaline earth metal cation, an organic amino cation, or ammonium; $R_3$ is hydrogen, an alkyl of from one to six carbon atoms which may be substituted by hydroxy phenyl or $CO_2R_6$; or a pharmaceutically acceptable acid addition salt thereof.

2. A compound according to claim 1 wherein X is CH.

3. A compound according to claim 1 wherein $R_1$ and $R_2$ are the same or different and are hydrogen or halogen.

4. A compound according to claim 3 wherein $R_1$ and $R_2$ are the same or different and are hydrogen or chlorine.

5. A compound according to claim 1 wherein n is an integer of from three to five.

6. A compound according to claim 1 wherein $R_4$ and $R_5$ are methyl.

7. A compound according to claim 1 wherein $R_6$ is hydrogen or alkyl of one to two carbon atoms.

8. A compound according to claim 1 and being 5-[4-(1H-benzimidazol-2-yl)phenoxy]-2,2-dimethyl-pentanoic acid methyl ester.

9. A compound according to claim 1 and being 5-[4-(1H-benzimidazol-2-yl)phenoxy]-2,2-dimethyl-pentanoic acid.

10. A compound according to claim 1 and being 7-[4-(1H-benzimidazol-2-yl)phenoxy]-2,2-dimethyl-heptanoic acid methyl ester.

11. A compound according to claim 1 and being 6-[4-(1H-benzimidazol-2-yl)phenoxy]-2,2-dimethyl-hexanoic acid methyl ester.

12. A compound according to claim 1 and being 8-[4-(1H-benzimidazol-2-yl)phenoxy]-2,2-dimethyloctanoic acid methyl ester.

13. A compound according to claim 1 and being 5-[4-(5-chloro-1H-benzimidazol-2-yl)phenoxy-2,2-dimethyl-pentanoic acid methyl ester.

14. A compound according to claim 1 and being 5-[4-(5,6-dimethyl-1H-benzimidazol-2-yl) phenoxy]-2,2-dimethyl-pentanoic acid methyl ester.

15. A compound according to claim 1 and being 7-[4-(5-chloro-1H-benzimidazol-2-yl)phenoxy-2,2-dimethyl-heptanoic acid methyl ester.

16. A compound according to claim 1 and being 5-[4-(5,6-dichloro-1H-benzimidazol-2-yl) phenoxy]-2,2-dimethyl-pentanoic acid methyl ester.

17. A compound according to claim 1 and being 2,2-dimethyl-5-[4-(5-methyl-1H-benzimidazol-2-yl)phenoxy]-pentanoic acid methyl ester trihydrate.

18. A compound according to claim 1 and being 2,2-dimethyl-5-[4-(1-methyl-1H-benzimidazol-2-yl)phenoxy]-pentanoic acid methyl ester.

19. A compound according to claim 1 and being 2-[4-[(5-methoxy-4,4-dimethyl-5oxopentyl)oxy]phenyl]-1H-benzimidazole-1-acetic acid ethyl ester.

20. A compound according to claim 1 and being 2,2-dimethyl-5-[4-[1-phenylmethyl)-1H-benzimidazol-2-yl]phenoxy]-pentanoic acid methyl ester.

21. A compound according to claim 1 and being 5-[4-[1-(-hydroxyethyl)-1H-benzimidazol-2-yl]-phenoxy]-2,2-dimethyl-pentanoic acid hydrate.

22. A compound according to claim 1 and being 2,2-dimethyl-5-[4-[1-(1-methylethyl)-1H-benzimidazol-2-yl]phenoxy]-pentanoic acid.

23. A compound according to claim 1 and being 2-[4-[(4-carboxy-4-methylpentyl)oxy]phenyl]-α, α-dimethyl-1-benzimidazole-1-pentanoic acid.

24. A compound according to claim 1 and being 2,2-dimethyl-7-[4-[1-(phenylmethyl)-1H-benzimidazol-2-yl]-heptanoic acid methyl ester.

25. A compound according to claim 1 and being 5-[4-(3H-imidazo[4,5-b]pyridin-2-yl)phenoxy]-2,2-dimethyl-pentanoic acid methyl ester.

26. A compound according to claim 1 and being 5-[4-(3H-imidazo[4,5-b]pyridin-2-yl)phenoxy]-2,2-dimethyl-pentanoic acid.

27. An antiarteriosclerotic pharmaceutical composition comprising an effective amount of a compound as defined in claim 1 in combination with a pharmaceutically acceptable carrier.

28. A method of treating arteriosclerosis in mammals which comprises administering to said mammals a pharmaceutical composition in accordance with claim 27 in unit dosage form.

* * * * *